United States Patent [19]

Katsoulis et al.

[11] Patent Number: 5,232,689
[45] Date of Patent: Aug. 3, 1993

[54] TRANSLUCENT ANTIPERSPIRANT COMPOSITIONS

[75] Inventors: Dimitris E. Katsoulis, Midland; Janet M. Smith, Bay City, both of Mich.

[73] Assignee: Dow Corning Corporation, Midland, Mich.

[21] Appl. No.: 742,669

[22] Filed: Aug. 7, 1991

Related U.S. Application Data

[63] Continuation-in-part of Ser. No. 631,309, Dec. 21, 1990, abandoned.

[51] Int. Cl.$^5$ .......................... A61K 7/34; A61K 7/38
[52] U.S. Cl. .................. 424/66; 424/DIG. 5; 424/68; 424/401
[58] Field of Search ............... 428/402.24; 424/401, 424/420, 476, 489, DIG. 5, 68, 66

[56] References Cited

U.S. PATENT DOCUMENTS

| | | | |
|---|---|---|---|
| 3,300,387 | 10/1962 | Kole | 167/90 |
| 4,369,173 | 1/1983 | Causland et al. | 424/401 |
| 4,425,328 | 1/1984 | Nabial | 424/66 |

FOREIGN PATENT DOCUMENTS

| | | | |
|---|---|---|---|
| 0175538 | 9/1985 | Japan | 428/402.24 |
| 1242634 | 10/1986 | Japan | 428/402.24 |
| 2052661 | 2/1990 | Japan | 428/402.24 |

*Primary Examiner*—Dale R. Ore
*Attorney, Agent, or Firm*—Sharon K. Severance

[57] ABSTRACT

Translucent antiperspirant compositions are comprised of an antiperspirant active in a gel base. The translucent antiperspirant composition is comprised of (A) 50 to 95% by weight of an anhydrous carrier liquid selected from volatile silicones, low viscosity silicones, anhydrous monoalcohols, polyalcohols, fatty alcohols, alcohol soluble emollients and mixtures thereof; (B) 5 to 20% by weight of a metal stearate; (C) 1 to 25% of an encapsulated antiperspirant active selected from an encapsulated aluminum salt, an encapsulated aluminum-zirconium salt and mixtures thereof and optionally (D) 0.5 to 10 weight percent of a silicone carboxy acid. The compositions do not leave a visible white residue when they are applied to the skin.

10 Claims, No Drawings ures thereof. The deodorant or antiperspirant sticks are claimed as being transparent however, there is nothing in the patent which exemplifies this claim.

TRANSLUCENT ANTIPERSPIRANT COMPOSITIONS

This application is a continuation-in-part of copending application Ser. No. 07/631,309 filed Dec. 21, 1990, now abandoned.

BACKGROUND OF THE INVENTION

In the past it has not been possible to form translucent antiperspirant stick compositions because of the physical and chemical characteristics of the antiperspirant active. Translucent gel bases, known in the art, are produced using a metal stearate (most commonly sodium stearate) as the gellant. The presence of an acid, such as an antiperspirant active, in the gel base interferes with the metal stearate and converts it to stearic acid which causes the stick to break down, become extremely soft or inhibit gellation.

Antiperspirant sticks known in the art are produced using waxy gellants such as stearyl alcohol, cetyl alcohol and hydrogenated caster oil. The acidity of the antiperspirant active does not interfere with or breakdown these gellants, however, the sticks are mostly white.

It is known in the art to produce transparent deodorant compositions since most deodorant actives do not interfere with the integrity of the gel base. For example, Canadian Patent 1196867 to Geria teaches a non aqueous transparent deodorant stick comprised of sodium stearate, propylene glycol, antimicrobial agents (deodorant actives) and ethanol. These sticks are shown to be stable and non-staining. Antiperspirant actives are not taught as a suitable additive.

EP Patent 107330 to Leubbe et al. teaches a clear cosmetic gel stick which can be used to deliver deodorants or other cosmetic materials. Delivery of antiperspirant actives is not taught. The clear gel sticks are comprised of an aliphatic, polyhydric alcohol, a soap, a hydro-alcoholic soluble emollient of the formula $R(OC_3H_6)_a(OC_2H_4)_bOH$, and water.

U.S. Pat. No. 4,440,742 to Marschner teaches deodorant stick compositions which comprise an alkali metal bi-carbonate as a deodorizing agent dissolved in a polyalcohol optionally mixed with a monoalcohol, solidified by an alkali metal salt of a saturated fatty acid gelling agent. Additional ingredients such as perfumes, colouring agents, ultraviolet absorbers can be added to enhance the color or improve the aesthetic value. The sticks may be transparent or opaque depending upon the amount of bicarbonate added and the particular ingredients employed. Antiperspirant stick compositions are not taught nor is antiperspirant active shown to be a suitable additive.

EP Patent 0291334 to Burger et al. teaches antiperspirant compositions in the form of a transparent stick. The antiperspirant compositions are comprised of an aluminum salt, a nonionic surfactant, a liquid oil which is immiscible with water. The transparent sticks are produced by combining an oil phase (liquid oil) and an aqueous phase (water, aluminum salt, and nonionic surfactant) where the components and quantities of the components are such the two phases have approximately the same refractive index. The nonionic surfactant includes the gellation.

U.S. Pat. No. 4,743,444 to McCall teaches deodorant or antiperspirant sticks. The sticks are comprised of a liquid base, benzylidene sorbitol, the astringent salt or deodorant active, fatty alcohol and optionally volatile silcone oil. The liquid base is selected from nonohydric alcohols, polyhydric alcohols, water or mixtures thereof. The deodorant or antiperspirant sticks are claimed as being transparent however, there is nothing in the patent which exemplifies this claim.

Translucent antiperspirant sticks known in the art have not been commercially viable because they are not aesthetically pleasing to the consumer. This invention overcomes that problem by producing an antiperspirant stick that contains antiperspirant actives and that are aesthetically pleasing to the consumer.

It is an object of this invention to show antiperspirant stick compositions that are translucent.

It is further an object of this invention to show antiperspirant compositions that are translucent and do not leave a visible white residue on the skin.

It is further an object of this invention to show translucent antiperspirant stick compositions wherein the stability of the stick is improved by the use of a silicone carboxy acid.

SUMMARY OF THE INVENTION

This invention pertains to translucent antiperspirant compositions which are comprised of an antiperspirant active in a gel base. The translucent antiperspirant composition is comprised of (A) 50 to 95% by weight of an anhydrous carrier liquid selected from volatile silicones, low viscosity silicones, anhydrous monoalcohols, polyalcohols, fatty alcohols, alcohol soluble emollients and mixtures thereof; (B) 5 to 20% by weight of a metal stearate; and (C) 1 to 25% by weight of an encapsulated antiperspirant active selected from an encapsulated aluminum salt, an encapsulated aluminum- zirconium salt and mixtures thereof.

A further aspect of this invention is antiperspirant stick compositions that have improved stability comprised of (A) 50 to 95% by weight of an anhydrous carrier liquid selected from volatile silicones, low viscosity silicones, anhydrous monoalcohols, polyalcohols, fatty alcohols, alcohol soluble emollients and mixtures thereof; (B) 5 to 20% by weight of a metal stearate; (C) 0.5 to 10% by weight of a silicone carboxy acid; and (D) 1 to 25% by weight of an encapsulated antiperspirant active selected from an encapsulated aluminum salt, an encapsulated aluminum- zirconium salt and mixtures thereof.

THE INVENTION

The instant invention pertains to translucent antiperspirant compositions which are comprised of a anhydrous liquid carrier, a metal stearate, encapsulated antiperspirant active and optionally a silicone carboxy acid. The translucent antiperspirant compositions are produced by combining together the anhydrous carrier liquid, the metal stearate and optionally the silicone carboxy acid (gel base) at a temperature of at least 60° C. and preferably at 80° C. The gel base mixture is held at a temperature of at least 80° C., preferably at temperature of 100° C. while the encapsulated antiperspirant active is added. The resulting mixture of the encapsulated antiperspirant active and gel base is then allowed to cool to room temperature with agitation preferably maintained until the gelling temperature.

The translucent antiperspirant composition may be formed into the antiperspirant stick at any point during the cooling, however to minimize settling of the antiperspirant active, it is preferred to form the antiperspirant stick when the temperature of the mixture is just above the temperature at which the mixture gels.

The translucent antiperspirant composition is comprised of 50 to 95% by weight of an anhydrous carrier liquid selected from volatile silicones, low viscosity silicones, anhydrous monoalcohols, polyalcohols, fatty alcohols, and alcohol soluble emollients and mixtures thereof.

The volatile silicones may be selected from linear and cyclic volatile silicones and mixtures thereof. It is well known in the art that volatile silicones are those that have a normal boiling point below 250° C.

The cyclic volatile silicones may be further exemplified by compounds having the formula

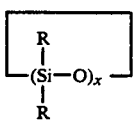
(I)

wherein each R is independently selected from an alkyl group containing 1 to 3 carbon atoms and an aryl group containing 6 to 10 carbon atoms and x has the value of 3 to 10. The preferred cyclic volatile silicones are where R is predominantly methyl and x is 4 to 5.

The linear volatile silicones may be further exemplified by compounds having the formula

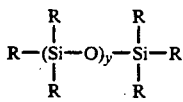
(II)

wherein each R is independently selected from an alkyl group containing 1 to 3 carbon atoms and an aryl group containing 6 to 10 carbon atoms and y has the value of 1 to 10. The preferred linear volatile silicones are where R is predominantly methyl and y is 1 to 2.

The linear and cyclic volatile silicones may be further exemplified by, but not limited to hexamethylcyclotrisiloxane, octamethylcyclotetrasiloxane, decamethylcyclopentasiloxane, dodecamethylcyclohexasiloxane, hexamethyldisiloxane, trimethylendblocked dimethylpolysiloxane, 0.65 cS dimethylpolysiloxane, octamethyltrisiloxane, decamethyltetrasiloxane, and mixtures thereof. A mixture comprising octamethylcyclotetrasiloxane, decamethylcyclopentasiloxane is the preferred volatile silicone.

The low viscosity silicones are selected from linear and cyclic silicone which have a viscosity of less than 1,000 centistokes and mixtures thereof. The cyclic low viscosity silicones may be exemplified by those compounds having the formula

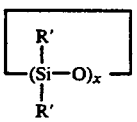
(III)

wherein each R' is independently selected from an alkyl group containing 1 to 10 carbon atoms and an aryl group containing 6 to 10 carbon atoms and x has the value of 3 to 10.

The linear low viscosity silicones may be exemplified by compounds having the formula

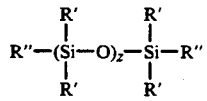
(IV)

wherein each R" is independently selected from an alkyl group containing 1 to 10 carbon atoms, an aryl group containing 6 to 10 carbon atoms, and an hydroxyl (—OH) group; R' is as described above; and z is such that the viscosity is less than 1,000 centistokes.

The low viscosity silicones may be further exemplified by, but not limited to, hydroxyl endblocked polydimethylsiloxanes, phenylmethyl fluids, 100 centistoke polydimethylsiloxane and others.

The anhydrous monoalcohols which are useful may be exemplified by, but not limited to ethanol, isopropanol and mixtures thereof. The preferred anhydrous monoalcohol is 200 proof ethanol.

Polyalcohols which are useful may be exemplified by, but not limited to, propylene glycol, trimethylene glycol, glycerol, sorbitol, 1,3 butanediol, 1,4 butanediol and mixtures thereof. The preferred polyalcohol is propylene glycol.

The fatty alcohols are selected from those compounds having the formula $$CH_3-R^1-CH_2-OH \qquad (V)$$

wherein $R^1$ is selected from linear and branched alkylene groups having 10 to 22 carbon atoms.

The fatty alcohols may be exemplified by, but not limited to, lauryl alcohol, myristyl alcohol, cetyl alcohol, isostearyl alcohol, and stearyl alcohol and mixtures thereof.

The preferred fatty alcohol is isostearyl alcohol.

The alcohol soluble emollients are selected from compounds having the formulas $$R^2(OC_3H_6)_m(OC_2H_4)_nOH \qquad (VI)$$

$$R^2(OC_2H_4)_nOH \qquad (VII)$$

and $$R^2(OC_3H_6)_mOH \qquad (VIII)$$

where $R^2$ is selected from the hydrogen atom and a hydrocarbon chain having 1 to 18 carbon atoms; m has the value of 3 to 26; n has the value of 3 to 26; and $m/(m+n) \leq 0.5$.

The alcohol soluble emollients may be exemplified by, but not limited to, PPG-10 cetyl ether, PEG-4, PEG-20 laurate, PEG-6-32, Poloxamer 335, PEG-5 cetyl ether, and PEG-3 myreth-3, PPG-3-myristyl ether, PPG-9 butyl ether, PPG-3 methyl ether, PPG-4 lauryl ether, PPG-11 stearyl ether (CFTA nomenclature) and mixtures thereof. Preferred alcohol soluble emollients are PEG-4, PPG-10 cetyl ether and mixtures thereof.

The translucent antiperspirant composition is further comprised of 5 to 20% by weight and preferably 8 to 12% by weight of a metal stearate. The metal stearate acts as a gellator for the antiperspirant compositions. The metal stearate is typically a solid at room temperature (i.e. 25° C.) and is typically an alkali metal or alkaline earth metal stearate. Metal stearates which may be useful in the instant invention may be exemplified by, but not limited to, sodium stearate, potassium stearate, aluminum monostearate and mixtures thereof. Sodium stearate is the preferred metal stearate.

The translucent antiperspirant composition is further comprised of an encapsulated antiperspirant active. The encapsulated antiperspirant active is added into the translucent antiperspirant stick composition at a level of 1 to 25% by weight and preferably 10 to 15% by weight.

The encapsulated antiperspirant actives comprise known antiperspirant actives such as aluminum chlorohydrate and aluminum-zirconium tetrachlorohydrate-glycinate contained in a shell comprising a carboxylic acid, carboxylic acid derivative, silicone carboxy acid or silicone carbocy acid derivative. It is theorized that the encapsulation of the antiperspirant active allows the antiperspirant active to be added into the gel base without effecting the clarity or integrity of the gel base.

The encapsulated antiperspirant actives useful in the instant invention are produced by (A) combining together, with agitation, an aqueous aluminum salt or an aqueous aluminum-zirconium salt, a non-water miscible hydrophobic liquid (herein referred to as hydrophobic liquid), and a carboxylate selected from carboxylic acids, alkali metal carboxylates, glyceryl carboxylates, carboxylic acid anhydrides, carboxylic acid chlorides, silicone carboxy acids, silicone carboxy acid derivatives and mixtures thereof; and (B) heating the mixture to a temperature (water distillation temperature) sufficient to remove substantially all of the free water. Some of the hydrophobic liquid may be removed during the heating because of an azeotrope that may formed between the hydrophobic liquid and the water. After the removal of the water, the encapsulated antiperspirant active precipitates out of the reaction medium. Typically, an increase in the temperature will occur when the distillation of the aqueous phase is complete. Upon completion of the distillation there should be enough fluid remaining to keep the encapsulated antiperspirant active free flowing. The encapsulated antiperspirant active can be recovered through separation means such as filtration.

The aqueous aluminum salts and the aqueous aluminum-zirconium salts useful in producing the encapsulated antiperspirant actives are those currently known in the art. The aluminum salts may be exemplified by aluminum halohydrates such as aluminum chlorohydrate, aluminum bromohydrate, and aluminum iodohydrate; aluminum nitrohydrate; and mixtures thereof. The aluminum salts useful in the instant invention may be further described as a standard (non-activated) or an activated salt. An activated salt, through compositional differences, is more efficacious when used in antiperspirant compositions.

The aluminum salts useful in the instant invention may be furthei described the formula $$Al_a(OH)_bX_c \qquad (IX)$$

where $1/3 \leq a/c \leq 2.2/1$; c has the value of 0 to 5.9; $3a = b + c$; and X is selected from Cl, Br, I and $NO_3$.

The aluminum-zirconium salts may be exemplified by aluminum-zirconium (amino acid) halohydrates such as aluminum-zirconium (glycine) chlorohydrate, aluminum-zirconium (glycine) bromohydrate, and aluminum-zirconium (glycine) iodohydrate and mixtures thereof. The aluminum-zirconium salts are typically buffered with an amino acid such as glycine. The aluminum-zirconium salts useful in the instant invention may be further described as a standard (non-activated) or an activated salt. An activated salt, through compositional differences, is more efficacious when used in antiperspirant compositions.

The aluminum-zirconium salts useful in the instant invention may be further described the formula $$Al_dZr_e(OH)_fX_g \qquad (X)$$

where d/e has the value of 0 to 20; e is greater than 0; $f+g = 3d+4e$; and X is selected from Cl, Br, I, and $NO_3$.

The aluminum and aluminum-zirconium salts are supplied as an aqueous solution containing greater than 0% by weight of the aluminum or aluminum-zirconium salt. The maximum amount of aluminum salt or aluminum-zirconium salt in the aqueous solution is dependent upon its solubility in water. Typically the aluminum salts are used as an aqueous solution comprising 10% to 50% by weight of the aluminum salt and typically the aluminum-zirconium salts are used as an aqueous solution comprising 10% to 40% by weight of the aluminum-zirconium salt. Aqueous solutions containing less than 10% by weight of the aluminum salt or aluminum-zirconium salt may be used to produce an encapsulated antiperspirant active, however, they are not economically advantageous. Aqueous solutions containing greater than 50% by weight of the aluminum salt and greater than 40% by weight of the aluminum-zirconium salt are not well known in the art however, they are useful when obtainable. The aqueous aluminum salts and aluminum-zirconium salts useful in the instant invention are commercially available or may be produced using methods known in the art.

Non-water miscible hydrophobic liquids useful in producing the encapsulated antiperspirant active may be selected from low viscosity silicone fluids, paraffin oils such as mineral oil, and mixtures thereof. The low viscosity silicones and further, low viscosity cyclic siloxanes are the preferred hydrophobic liquid.

Low viscosity silicones useful in the instant invention are selected from cyclic and linear silicones and mixtures thereof which have a viscosity of less than 1,000 centistokes. The cyclic low viscosity silicones may be exemplified by compounds having the formulas (I) and (III), described above.

The cyclic low viscosity silicones may be further exemplified by, but not limited to hexamethylcyclotrisiloxane, octamethylcyclotetrasiloxane, decamethylcyclopentasiloxane, dodecamethylcyclohexasiloxane and mixtures thereof.

The linear low viscosity silicones may be exemplified by compounds having the formulas (II) and (IV), described above.

The linear low viscosity silicones may be further exemplified by, but not limited to, trimethylendblocked dimethylpolysiloxane fluids, 5, 10, 25 and 50 cS dimethylpolysiloxane fluids, hydroxyl endblocked polydimethylsiloxane fluids, octamethyltrisiloxane, decamethyltetrasiloxane, and mixtures thereof.

The carboxylates useful in producing the encapsulated antiperspirant actives may be selected from carboxylic acids, silicone carboxylic acids, carboxylic acid anhydrides, carboxylic acid chlorides, alkali metal carboxylates, glyceryl carboxylates, and mixtures thereof.

The carboxylic acids, alkali metal carboxylates, glyceryl carboxylates, carboxylic acid anhydrides, carboxylic acid chlorides may be exemplified by compounds or mixtures of compounds having the formulas

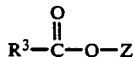 (XI)

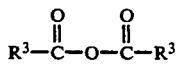 (XII)

and

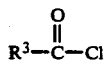 (XIII)

wherein $R^3$ is selected from the group consisting of a saturated or unsaturated, branched or linear alkyl group consisting of at least 2 carbon atoms and a substituted or unsubstituted phenyl group consisting of at least 6 carbon atoms; and Z is selected from the hydrogen atom, alkali metals, and glyceryl.

$R^3$ may be further exemplified by ethyl, propyl, octyl, decyl, undecyl, pentadecyl, hexadecyl, octadecyl, doeicosyl, phenyl, phenyl ethylene, methyl ethyl phenylene and others. Z may be further exemplified by the hydrogen atom, sodium, potassium, $-CH_2CH(OH)CH_2OH$, and $-CH(OH)CH_2OH$.

The carboxylic acids may be further exemplified by, but are not limited to, butyric acid, caprylic acid, lauric acid, palmitic acid, stearic acid, behenic acid, oleic acid, linoleic acid, linolenic acid and phenylacetic acid. The alkali metal carboxylates may be further exemplified by sodium stearate, sodium palmitate, and potassium stearate. The glyceryl carboxylates may be further exemplified by glyceryl monostearate. The acid anhydrides and acid chlorides may be further exemplified by, but not limited to stearic anhydride, palmitic anhydride, lauric anhydride, stearoyl chloride, myristoyl chloride, and octanoyl chloride.

The silicone carboxy acids and silicone carboxy acid derivatives useful in producing the encapsulated antiperspirant active may be exemplified by silicone carboxy acids, silicone carboxy acid derivatives or mixtures of thereof having the formula:

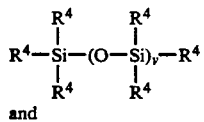 (XIV)

and

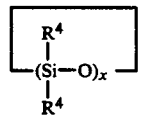 (XV)

wherein each $R^4$ is independently selected from an alkyl group containing 1 to 30 carbon atoms, an aryl group containing 6 to 10 carbon atoms, an alkaryl group containing 7 to 20 carbon atoms, an aralkyl group containing 7 to 20 carbon atoms, a hydroxyl group, and a carboxy functional group having at least 2 carbon atoms, with the provision that at least one $R^4$ group is a carboxy functional group; v has the value of 1 to 1,000 and x has the value of 3 to 10.

$R^4$ may be a carboxy functional group wherein a carboxy functional group may be defined as a monovalent radical which contains a $-COOH$, $-C(O)-O-C(O)-$, $-C(O)Cl$, $-C(O)OQ$, $-C(O)OW$, or $-C(O)SiR_5$ radical, where Q is an alkali metal, W is glyceryl and $R^5$ is selected from an alkyl group containing 1 to 30 carbon atoms, an aryl group containing 6 to 10 carbon atoms, an alkaryl group containing 7 to 20 carbon atoms, and an aralkyl group containing 7 to 20 carbon atoms; and is attached to a silicon atom of the main molecular chain by a divalent linking group. Attachment to the silicon atom is through a silicon to carbon bond. The divalent linking group is an alkylene group containing at least 2 carbon atoms. There must be at least one carboxy functional group on the molecule. The carboxy functional group(s) may be located on the terminal ends of the polymer and/or along the polymer backbone.

The silicone carboxys useful in producing the encapsulated antiperspirant active include silicone carboxy acids, alkali metal silicone carboxylates, silicone acid chlorides, silicone acid anhydrides, glyceryl silicone carboxylates and mixtures thereof.

For the carboxylates to be useful in producing the encapsulated antiperspirant active it is necessary for the carboxylate to be soluble in the hydrophobic liquid and/or to have a melting point less than the water distillation temperature and further, the carboxylate must not be completely distillable at the water distillation temperature. When using a metal carboxylate it may be necessary to add a co-solvent, such as water, to completely dissolve the alkali metal carboxylate. The preferred carboxylate is stearic acid as it is a cosmetically acceptable ingredient and it has the acceptable properties to make it useful.

The encapsulated antiperspirant actives are formed by combining at least 14 millimoles of carboxylate for every 100 parts of aluminum or aluminum-zirconium salt, and at least 1 part of hydrophobic liquid for every part of water. It is preferred to use between 20 to 200 millimoles of carboxylate per every 100 parts of aluminum or aluminum-zirconium salt and at least 1.25 parts hydrophobic liquid per every part of water. It may be possible to use less than one part of hydrophobic liquid for every part of water if the amount of hydrophobic liquid lost in the distillation azeotrope is replaced during the course of the reaction.

The aqueous aluminum or aluminum-zirconium salt, carboxylate and hydrophobic liquid are combined and heated, with agitation, to a temperature sufficient to remove substantially all of the free water from the solution (water distillation temperature). Typically temperatures greater than 100° C., preferably 110° to 130° C., at atmospheric pressure are useful for removing the water. When the water has been removed the temperature will rise above the water distillation temperature. It is preferred that the temperature does not exceed 150° C. for an extended period of time. Temperatures which exceed 150° C. for an extended period of time may be detrimental to the encapsulant and lead to fragmentation or cracking of the shell and possibly the conversion of the aluminum or aluminum-zirconium salt into an aluminum or aluminum-zirconium oxide. Pressures greater or less than atmospheric pressure can be employed in the method of the instant invention thereby allowing the mixture to be heated to higher or lower temperatures for the removal of the water. It is essential that the water be removed during the heating step. Merely heating to temperatures greater than 100° C.

while refluxing, or containing the water otherwise, will not result in an encapsulated salt. Typically, the completion of the water removal will be indicated by an increase in the temperature above the water distillation temperature.

After the removal of the free water from the mixture, the encapsulated antiperspirant actives precipitate out of the reaction medium. The encapsulated antiperspirant actives are typically recovered from the reaction medium by filtration means such as gravimetric, pressure or vacuum filters or by other separatiom means such as decanting or centrifuging. Filtration means will vary depending on the batch size. It is preferred to recover the encapsulated antiperspirant actives from the reaction medium at a temperature at or above the temperature at which the carboxylate is a liquid. It is further preferred to recover the encapsulated antiperspirant actives from the reaction medium using filtration.

After the encapsulated antiperspirant actives have been recovered from the reaction medium, they may be optionally washed using a hydrophobic solvent to remove any excess carboxylate that might be adhered to the shells. If the carboxylate is not a liquid at room temperature it may be necessary to heat the hydrophobic solvent, during the wash, to a temperature at which the carboxylate is a liquid.

The translucent antiperspirant composition optionally comprises 0.5 to 10 percent by weight, preferably 2 to 7 weight percent of a silicone carboxy acid. The silicone carboxy acid is optionally added into the translucent antiperspirant composition to further improve the stability of the sticks. The silicone carboxy acids useful in the instant invention those silicone carboxy acids or mixtures of silicone carboxy acids having the formula (XIV) and (XV) described above wherein the carboxy functional group is —COOH.

It is important for the components in the gel base of the translucent antiperspirant compositions to be essentially free of water. The shells of the encapsulated antiperspirant actives, in the presence of moisture, open up and release the antiperspirant active. Presence of water in the components of the gel base will open up the shell of the encapsulated salt and release the acidic antiperspirant active, making it available to react with the metal stearate. This will result in a reduction or loss of the integrity of the antiperspirant composition. It is theorized that minor amounts of water in the gel base components or that which may be absorbed into the stick from the atmosphere will only affect the stability of the stick over time.

Additional ingredients may be added to improve the aesthetics, emolliency or stability of the stick as long as they are anhydrous and do not effect the clarity of the stick. These additional ingredients may include perfumes, deodorants, preservatives, sunscreens, emollients, surfactants, coloring agents, amines and others. Typically the additives are present at levels of 0-10% by weight of the composition.

The translucent antiperspirant compositions are produced by combining together the ingredients of the gel base at a temperature of at least 60° C. and preferably at about 80° C. The gel base mixture is held at a temperature of at least 80° C., preferably at temperature of about 100° C. while the encapsulated antiperspirant active is added. The resulting mixture of the encapsulated antiperspirant active and gel base is then allowed to cool to room temperature. It is preferred to maintain agitation until the gelling point to minimize the settling of the encapsulated antiperspirant active.

The preferred method for producing the antiperspirant compositions is to add the metal stearate to part of or all of the anhydrous carrier liquid and heat to a temperature of at least 70° C. to solubilize the metal stearate. The remaining anhydrous carrier liquid is then added to the gel base mixture at a temperature of at least 60° C. The gel base mixture is maintained with agitation at a temperature above 80° C., preferably at temperature of about 100° C. while the encapsulated antiperspirant active is added. The resulting mixture of the encapsulated antiperspirant active and gel base is then allowed to cool to room temperature. Agitation, which is used to prevent settling of the encapsulated antiperspirant active, is maintained until the gelling (solidification) point.

The temperature at which the translucent antiperspirant composition will gel is dependent upon the individual components in the gel base. However, one skilled in the art will be able to easily determine the gel temperature.

The translucent antiperspirant compositions may be formed into antiperspirant sticks by methods known in the art. It is preferred to form the antiperspirant sticks when the translucent antiperspirant composition is at a temperature slightly higher than the temperature at which it gels.

The silicone carboxy acid, when used, can be added into the translucent antiperspirant stick at any point prior to the solidification of the composition. It is preferred to add the silicone carboxy acid into the translucent antiperspirant composition prior to the addition of the encapsulated active.

In addition to being translucent, the antiperspirant compositions also do not leave a visible white residue when applied to the skin.

So that those skilled in the art can understand and appreciate the invention taught herein, the following examples are presented, it being understood that these examples should not limit the scope of this invention over the limitations found in the claims attached hereto.

Translucency was determined by placing a thin wafer of the antiperspirant stick between two parts of a demountable rectangular cell, supplied by Starna Cells, Inc. having a path length of 0.05 millimeters (mm). Mild pressure was applied to the cell to ensure that the gel filled the entire space. This provided an identical path length for all the samples. The absorbance of the samples was measured using a Spectronic 1201 Computer Operated Dual Beam Scanning Spectrophotometer at 700 nanometers (nm) to 400 nm wavelengths. Translucency is represented when the measured absorbance is less than 1.0.

The term "parts" referred to herein means parts by weight.

PREP EXAMPLE 1

300 grams of a mixture comprised of octamethylcyclotetrasiloxane and decamethylcyclopentasiloxane and 11.88 grams of stearic acid were combined in a 1 L round bottom flask equipped with a paddle-blade agitator, a water cooled condenser and a 1 L round bottom receiver and heated to 67° C. 300 grams of aqueous Aluminum-Zirconium Tetrachlorhydrex-Gly (35% solids), heated to 70° C., was added to the stearic acid solution, with agitation. The mixture was heated for approximately 2.25 hours, while distilling off the water, maintaining a temperature around 110° C. The reaction was stopped when the pot temperature reached approximately 122° C. and no more water was observed to be distilling off. The mixture was then vacuum filtered (while hot, ~122° C.), using a Buchner funnel, to recover 108.6 grams of the encapsulated aluminum-zirconium salt. The beads were re-dissolved in 100 grams of a mixture comprised of octamethylcyclotetrasiloxane and decamethylcyclopentasiloxane and heated to 70° C. and filtered again. 104.1 grams of encapsulated aluminum-zirconium salt was recovered after the second filtration.

The encapsulated aluminum-zirconium salts were mostly spheres of varying sizes.

PREP EXAMPLE 2

750 grams of a mixture comprised of octamethylcyclotetrasiloxane and decamethylcyclopentasiloxane and 31.5 grams of stearic acid were combined in a 1 L round bottom flask equipped with a paddle-blade agitator, a water cooled condenser and a 1 L round bottom receiver and heated to 70° C. 750 grams of aqueous Aluminum-Zirconium Tetrachlorhydrex-Gly (35% solids) was added to the stearic acid solution, with agitation while maintaining a temperature around 70° C. The mixture was heated for approximately 6.5 hours, while distilling off the water, maintaining a temperature around 110° C. The reaction was stopped when the pot temperature reached approximately 115° C. and no more water was observed to be distilling off. The mixture was then vacuum filtered (while hot, ~70° C.), using a Buchner funnel, to recover the encapsulated aluminum-zirconium salt.

PREP EXAMPLE 3

1,125 grams of a mixture comprised of octamethylcyclotetrasiloxane and decamethylcyclopentasiloxane and 47.25 grams of stearic acid were combined in a 3 L round bottom flask equipped with a paddle-blade agitator, a water cooled condenser and a 2 L round bottom receiver and heated to 70° C. 1,125 grams of aqueous Aluminum-Zirconium Tetrachlorhydrex-Gly (35% solids) was added to the stearic acid solution, with agitation while maintaining a temperature around 70° C. The mixture was heated for approximately 5 hours, while distilling off the water, maintaining a temperature around 110° C. The reaction was stopped when the pot temperature reached approximately 130° C. and no more water was observed to be distilling off. The mixture was then vacuum filtered (while hot, ~99° C.), using a Buchner funnel, to recover the encapsulated aluminum-zirconium salt. The beads were redissolved in 1,000 grams of a mixture comprised of octamethylcyclotetrasiloxane and decamethylcyclopentasiloxane and heated to 70° C. and filtered again.

PREP EXAMPLE 4

In a 4000 ml beaker 2,000 grams of a mixture comprised of octamethylcyclotetrasiloxane and decamethylcyclopentasiloxane and 40 grams of a stearic acid were combined and heated until the acid dissolved. 1,000 grams of aqueous aluminum chlorohydrate (50% solids) was added and the mixture heated to approximately 100° C., with agitation, to boil off any water. Once all of the water boiled off, material encapsulated to fine, round particle. An encapsulated aluminum chlorohydrate salt compound resulted.

PREP EXAMPLE 5

A clear gel base was prepared by combining 12.5 parts of propylene glycol, 7.8 parts of PEG-4 and 10.4 parts of sodium stearate and heating the mixture until the sodium stearate dissolved (approximately 80° C.). 31.2 parts of cyclomethicone 20.3 parts of isostearyl alcohol, 10.4 parts of PPG-10 cetyl ether, and 7.8 parts of ethanol were combined in separate vessel and heated to 65° C. The two mixtures were combined with stirring and maintained at 80° C.

EXAMPLE 1

50 grams of the clear base gel prepared in Prep Example 5 was poured into a stick form and allowed to cool to room temperature. It was a solid at room temperature.

EXAMPLE 2

A translucent antiperspirant stick was formed by mixing 45 grams of the clear gel base prepared in Prep Example 5 with 5 grams of the encapsulated aluminum-zirconium salt prepared in Prep Example 1. The mixture was heated to 100° C. and poured into a stick form. Mild stirring was maintained until the mixture began to solidify. The mixture was a solid at room temperature.

EXAMPLE 3

A translucent antiperspirant stick was formed by mixing 42.5 grams of the clear gel base prepared in Prep Example 5 with 7.5 grams of the encapsulated aluminum zirconium salt prepared in Prep Example 2. The mixture was heated to 100° C. and poured into a stick form. Mild stirring was maintained until the mixture began to solidify. The mixture was a solid at room temperature.

EXAMPLE 4

A translucent antiperspirant stick was formed by mixing 40.0 grams of the clear gel base prepared in Prep Example 5 with 10.0 grams of the encapsulated aluminum-zirconium salt prepared in Prep Example 2. The mixture was heated to 100° C. and poured into a stick form. Mild stirring was maintained until the mixture began to solidify. The mixture was a solid at room temperature.

EXAMPLE 5

A translucent antiperspirant stick was formed by mixing 36.0 grams of the clear gel base prepared in Prep Example 5 with 4.0 grams of the encapsulated aluminum salt prepared in Prep Example 4. The mixture was heated to 100° C. and poured into a stick form. Mild stirring was maintained until the mixture began to solidify. The mixture was a solid at room temperature.

COMPARATIVE EXAMPLE 1

An antiperspirant stick was produced by heating 55 parts of cyclomethicone and 20 parts of stearyl alcohol to 65° C. with stirring. 2 parts of PPG-14 butyl ether was then added with continued stirring followed by 1 part of hydrogenated caster oil, 2 pars of talc, and 20 parts of the encapsulated aluminum-zirconium salt prepared in Prep Example 1. The mixture was cooled to 53° C. and cast into a stick.

EXAMPLE 6

The antiperspirant sticks were measured for translucency by placing a thin wafer (0.05 mm) of material between two glass cells and measuring the absorbance from 700 to 450 nm wavelengths. Several commercially available materials were used for comparison. Absorbance at 600 and 450 nm is reported in Table 1. A value of less than 1.000 at both values represents translucency. The samples may be described as follows:

Sample A: The gel base without any antiperspirant salt produced Example 1.
Sample B: The antiperspirant stick produced in Example 2.
Sample C: The antiperspirant stick produced in Example 3.
Sample D: The antiperspirant stick produced in Example 4.
Sample E: The antiperspirant stick produced in Example 5.
Sample F: The antiperspirant stick produced in Comparative Example 1.
Sample G: A commercially available deodorant stick.
Sample H: A commercially available deodorant stick.
Sample I: A commercially available antiperspirant stick.
Sample J: A commercially available antiperspirant stick.
Sample K: A commercially available antiperspirant stick.

TABLE 1

| Sample | Absorbance 600 nm | 450 nm |
|---|---|---|
| A | 0.020 | 0.008 |
| B | 0.102 | 0.117 |
| C | 0.423 | 0.469 |
| D | 0.621 | 0.721 |
| E | 0.575 | 0.526 |
| F | 2.257 | 2.341 |
| G | 0.096 | 0.207 |
| H | 0.409 | 0.503 |
| I | 1.566 | 1.829 |
| J | 2.488 | 2.533 |
| K | 2.543 | 2.667 |

EXAMPLE 7

The non-whitening properties was tested for Samples A, D, E, G, I, J (Example 6) by applying a small quantity (approximately 0.01 grams) to a 4.25"×4.25" glossy black ceramic tile manufactured by American Olean Tile Company and visually determining the whiteness of the residue after 5 and 30 minutes of drying. The non-whitening properties were also tested by applying the stick to a 1.25" square section of a forearm (Caucasian) and visually judging the whiteness of the residue after 5 and 30 minutes of drying. The whiteness of the residue was rated on a scale of 1 to 5 with 1 representing no white residue visible and 5 representing a strong white residue visible. Results of both tests are given in Table 2.

TABLE 2

| Sample | Black Tile* 5 min. | 30 min. | Forearm 5 min. | 30 min. |
|---|---|---|---|---|
| A | 1 | 1.16 | 1 | 1 |
| D | 1 | 1 | 1 | 1 |
| E | 1.5 | 1.5 | — | — |
| G | 1.5 | 2.33 | 1 | 1 |
| I | 2 | 3.66 | 2 | 4 |
| J | 1.5 | 2.66 | 1.5 | 2 |

*Average of three values

EXAMPLE 8

A translucent antiperspirant stick was prepared by combining 11.25 percent of propylene glycol, 7.0 percent of PEG-4 and 9.25 percent of sodium stearate and heating the mixture until the sodium stearate dissolved (approximately 80° C.). 28 percent of cyclomethicone 18.25 percent of isostearyl alcohol, 9.25 percent of PPG-10 cetyl ether, and 7.0 percent of ethanol were combined in separate vessel and heated to 65° C. The two mixtures were combined with stirring and maintained at 80° C. 10 percent of an encapsulated aluminum-zirconium tetrachloro-hydrex glycinate was added. The mixture was poured into a stick form and allowed to cool to room temperature. The stick failed (liquified) after 6 weeks at room temperature.

Another translucent antiperspirant stick was prepared by combining 10.7 weight percent of propylene glycol, 6.7 weight percent of PEG-4 and 9.0 weight percent of sodium stearate and heating the mixture until the sodium stearate dissolved (approximately 80° C.). 26.9 weight percent of cyclomethicone, 17.5 weight percent of isostearyl alcohol, 9.0 weight percent of PPG-10 cetyl ether, 6.7 weight percent of ethanol and 3.6 weight percent of a silicone carboxy acid having the formula

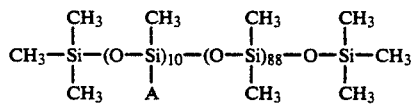

where A is $-CH_2-CH(CH_3)COOH$; were combined in separate vessel and heated to 65° C. The two mixtures were combined with stirring and maintained at 80° C. 10 weight percent of an encapsulated aluminum-zirconium tetrachlorohydrex glycinate was added. The mixture was poured into a stick form and allowed to cool to room temperature. The stick did not show any signs of deterioration after 2 months at room temperature.

EXAMPLE 9

A translucent antiperspirant stick was prepared by combining 12.0 parts of propylene glycol, 7.5 parts of PEG-4 and 10.0 parts of sodium stearate and heating the mixture until the sodium stearate dissolved (approximately 80° C.). 30.0 parts of cyclomethicone 19.5 parts of isostearyl alcohol, 10.0 parts of PPG-10 cetyl ether, and 7.8 parts of ethanol were combined in separate vessel and heated to 65° C. The two mixtures were combined with stirring and maintained at 80° C. 5 parts of an encapsulated aluminum-zirconium tetrachlorohydrex glycinate was added to the gel base. The mixture was poured into a stick form and allowed to cool to room temperature. The stick failed (liquified) after 2 weeks at room temperature.

Another translucent antiperspirant stick was prepared by combining 12.0 parts of propylene glycol, 7.5 parts of PEG-4 and 10.0 parts of sodium stearate and heating the mixture until the sodium stearate dissolved (approximately 80° C.). 30.0 parts of cyclomethicone, 19.5 parts of isostearyl alcohol, 10.0 parts of PPG-10 cetyl ether, 7.5 parts of ethanol and 4.0 parts of a silicone carboxy acid having the formula

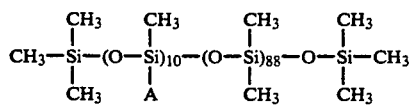

where A is -CH$_2$-CH(CH$_3$)COOH; were combined in separate vessel and heated to 65° C. The two mixtures were combined with stirring and maintained at 80° C. 5 parts of an encapsulated aluminum-zirconium tetrachlorohydrex glycinate was added. The mixture was poured into a stick form and allowed to cool to room temperature. The stick did not show any signs of deterioration after 8 months at room temperature.

What is claimed is:

1. A translucent antiperspirant composition comprising
   (A) 50 to 95% by weight of an anhydrous carrier liquid selected from the group consisting of volatile silicone, low viscosity silicone, anhydrous monoalcohol, polyalcohol, fatty alcohol, alcohol soluble emollient and mixtures thereof;
   (B) 5 to 20% by weight of a metal stearate; and
   (C) 1 to 25% of an encapsulated antiperspirant active wherein the encapsulated antiperspirant active comprises
      (i) an antiperspirant active selected from the group consisting of aluminum salt, aluminum-zirconium salt and mixtures thereof; contained in a shell comprising
      (ii) a carboxylate or a mixture of carboxylates selected from the group consisting of carboxylates having the formula

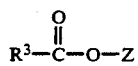

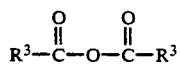

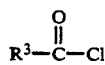

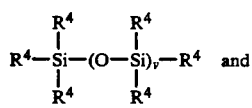

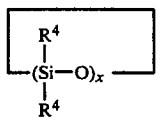

wherein

R$^3$ is selected from the group consisting of a saturated or unsaturated, branched or linear alkyl group consisting of at least 2 carbon atoms and a substituted or unsubstituted phenyl group consisting of at least 6 carbon atoms;

Z is selected from the group consisting of the hydrogen atom, alkali metals, and glyceryl;

each R$^4$ is independently selected from the group consisting of an alkyl group containing 1 to 30 carbon atoms, an aryl group containing 6 to 10 carbon atoms, an alkaryl group containing 7 to 20 carbon atoms, an aralkyl group containing 7 to 20 carbon atoms, a hydroxyl group and a carboxy functional group having at least 2 carbon atom, with the provision that at least one R$^4$ group be a carboxy functional group;

v has the value of 1 to 1,000; and x has the value of 3 to 10.

2. A composition as claimed in claim 1 wherein the metal stearate is sodium stearate.

3. A composition as claimed in claim 1 wherein the antiperspirant active is an aluminum salt.

4. A composition as claimed in claim 1 wherein the antiperspirant active is an aluminum-zirconium salt.

5. The composition as claimed in claim 1 which additionally contains 0.5 to 10 weight percent of a silicone carboxy acid.

6. The composition as claimed in claim 5 wherein the silicone carboxy acid is

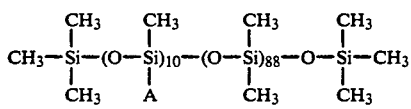

where A is —CH$_2$—CH(CH$_3$)COOH.

7. A method of inhibiting perspiration by applying the composition as claimed in claim 1 to the skin.

8. A method of inhibiting perspiration by applying the composition as claimed in claim 5 to the skin.

9. A method of applying the composition as claimed in claim 1 to the skin wherein a residue is not visible on the skin after the application.

10. A method of applying the composition as claimed in claim 5 to the skin wherein a residue is not visible on the skin after the application.

* * * * *